(12) United States Patent
Mendelsohn et al.

(10) Patent No.: US 9,814,867 B2
(45) Date of Patent: Nov. 14, 2017

(54) DEVICE HAVING TITANIA NANOTUBE MEMBRANE FOR DRUG DELIVERY

(71) Applicant: Nano Precision Medical, Inc., Emeryville, CA (US)

(72) Inventors: Adam D. Mendelsohn, San Francisco, CA (US); Kathleen E. Fischer, Oakland, CA (US); Lily H. Peng, San Francisco, CA (US); William G. Fischer, Oakland, CA (US)

(73) Assignee: NANO PRECISION MEDICAL, INC., Emeryville, CA (US)

( * ) Notice: Subject to any disclaimer, the term of this patent is extended or adjusted under 35 U.S.C. 154(b) by 404 days.

(21) Appl. No.: 14/362,554

(22) PCT Filed: Dec. 5, 2012

(86) PCT No.: PCT/US2012/067868
§ 371 (c)(1),
(2) Date: Jun. 3, 2014

(87) PCT Pub. No.: WO2013/085951
PCT Pub. Date: Jun. 13, 2013

(65) Prior Publication Data
US 2014/0371687 A1    Dec. 18, 2014

Related U.S. Application Data

(60) Provisional application No. 61/566,810, filed on Dec. 5, 2011.

(51) Int. Cl.
*A61M 31/00* (2006.01)
*A61K 38/21* (2006.01)
(Continued)

(52) U.S. Cl.
CPC ......... *A61M 31/002* (2013.01); *A61K 9/0024* (2013.01); *A61K 9/0092* (2013.01);
(Continued)

(58) Field of Classification Search
None
See application file for complete search history.

(56) References Cited

U.S. PATENT DOCUMENTS

| 5,972,369 A | 10/1999 | Roorda et al. |
| 2009/0232870 A1 | 9/2009 | Srivastava et al. |

(Continued)

FOREIGN PATENT DOCUMENTS

| CN | 101191248 A | 6/2008 |
| CN | 101550581 A | 10/2009 |

(Continued)

OTHER PUBLICATIONS

European Search Report for European Application No. 12854742.9 dated Aug. 3, 2015.
(Continued)

*Primary Examiner* — Vera Katz
(74) *Attorney, Agent, or Firm* — Kilpatrick Townsend and Stockton LLP

(57) ABSTRACT

The present invention provides a device including a titania nanotube membrane having a plurality of titania nanotubes on a titanium substrate where the titania nanotubes are open at both ends and capable of allowing diffusion of liquids or solids from one side of the membrane to the other through the titania nanotubes. Methods of making the titania nanotube membrane are also provided.

25 Claims, 5 Drawing Sheets

(51) Int. Cl.
| | |
|---|---|
| A61K 9/48 | (2006.01) |
| C25D 11/34 | (2006.01) |
| C25D 5/48 | (2006.01) |
| C25D 5/50 | (2006.01) |
| C25D 11/26 | (2006.01) |
| B82Y 30/00 | (2011.01) |
| A61K 9/00 | (2006.01) |

(52) U.S. Cl.
CPC .......... *A61K 9/4808* (2013.01); *A61K 38/212* (2013.01); *B82Y 30/00* (2013.01); *C25D 5/48* (2013.01); *C25D 5/50* (2013.01); *C25D 11/26* (2013.01); *C25D 11/34* (2013.01); *F04C 2270/041* (2013.01)

(56) References Cited

U.S. PATENT DOCUMENTS

2010/0044630 A1* 2/2010 Kang .................. B82Y 30/00
252/182.33
2010/0187172 A1 7/2010 Paulose et al.
2010/0213046 A1 8/2010 Grimes et al.
2010/0269894 A1* 10/2010 Misra ..................... B82Y 20/00
136/252

FOREIGN PATENT DOCUMENTS

| JP | 2005502426 | 1/2005 |
|---|---|---|
| WO | WO03/024357 | 3/2003 |

OTHER PUBLICATIONS

International Search Report and Written Opinion for PCT/US2012/067868 dated Apr. 5, 2013.
English Translation for CN101550581 dated Oct. 15, 2015.
Office Action for China Application No. 201280059539.3 dated Aug. 25, 2015 with English abstract.
Gultepe et al., "Nanoporous inorganic membranes or coatings for sustained drug delivery in implantable devices", Advanced Drug Delivery Reviews 62, 2010, pp. 305-315.

\* cited by examiner

DEVICE HAVING TITANIA NANOTUBE MEMBRANE FOR DRUG DELIVERY

CROSS-REFERENCES TO RELATED APPLICATIONS

This application is the U.S. National Stage Entry under §371 of International Application No. PCT/US2012/067868, filed Dec. 5, 2012, which claims priority to U.S. Provisional Application No. 61/566,810, filed Dec. 5, 2011, which is incorporated in its entirety herein for all purposes.

BACKGROUND OF THE INVENTION

Current injectable drug delivery therapies have debilitating side effects which significantly decrease quality of life for patients. As an example, patients receiving Interferon-alpha (IFN-a) treatment for hepatitis C (HCV) report that the side effects of their treatment are so severe that they are often unable to work. As a result of the debilitating effects of many injected therapies including IFN-a, patients are often not prescribed treatment until damaging effects of the disease have become severe, such as acute liver inflammation for people with HCV. Patients are required to inject themselves with a substance that they know will make them feel very ill for several days. Consequently, patients are disinclined to take their treatments as prescribed, and some cease treatment prematurely, adversely affecting their therapy. Many of the side effects from the interferon therapy are associated with the spike in drug concentration immediately following an injection. Ideally, IFN-α would enter the patient at a constant-rate, thereby reducing side effects. Recent advances in implantable titania nanoporous membranes have produced a novel method to control the release of macromolecules, eliminating the concentration spike associated with an injection. Furthermore, subcutaneously implanted devices can increase patient compliance, thereby increasing treatment efficacy while simultaneously reducing side effects. Surprisingly, the present invention meets this and other needs.

BRIEF SUMMARY OF THE INVENTION

In one embodiment, the present invention provides a device having a capsule suitable for implantation. The device also includes a reservoir encapsulated by the capsule, wherein the reservoir is suitable for containing a therapeutic agent. The device also includes a titania nanotube membrane on a titanium substrate, wherein the titanium substrate is attached to the capsule such that the titanium substrate is in contact with the reservoir, wherein the titania nanotube membrane comprises a plurality of titania nanotubes in fluid contact with the reservoir. The device is such that the plurality of titania nanotubes is the only diffusion pathway out of the reservoir for the therapeutic agent.

In another embodiment, the present invention provides a method of preparing a titania nanotube membrane, the method including growing a plurality of titania nanotubes on a first side of a titanium substrate under anodization conditions, such that a first end of each nanotube is closed and attached to the titanium substrate and a second end of each nanotube is open. The method also includes etching the titanium substrate on the side opposite the first side, under conditions sufficient to open the first end of a first group of the titania nanotubes, thereby preparing the titania nanotube membrane.

In another embodiment, the present invention provides a titania nanotube membrane prepared by the process above.

In another embodiment, the present invention provides a titania nanotube membrane having a plurality of titania nanotubes on a titanium substrate, wherein each nanotube has a first and a second end such that both the first and second ends of a first group of the titania nanotubes are open.

DETAILED DESCRIPTION OF THE INVENTION

I. General

Figure 1:
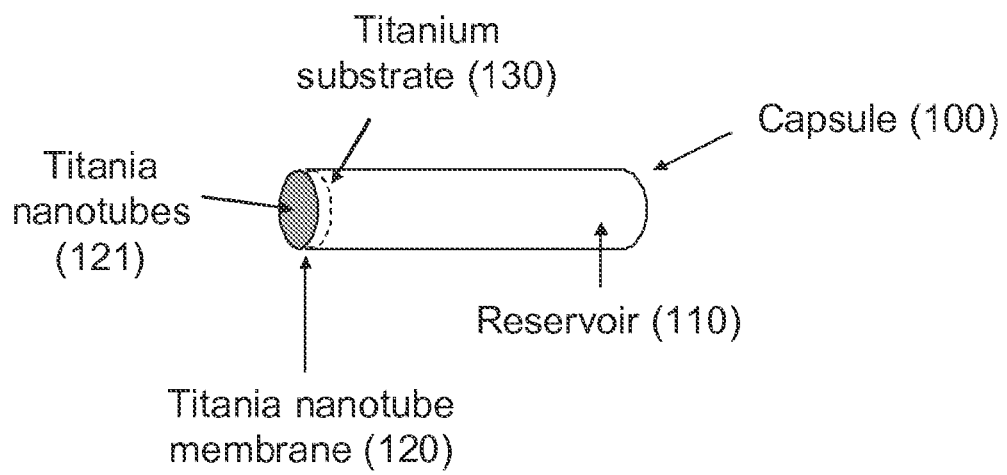
FIG. 1 shows one embodiments of the device of the present invention, with a capsule (100), a reservoir (110) encapsulated by the capsule, a titania nanotube membrane (120) in contact with the reservoir, where the titania nanotube membrane is on a titanium substrate (130), and where the titania nanotube membrane includes a plurality of titania nanotubes (121).

The present invention provides a drug delivery device having a plurality of titania nanotubes forming a titania nanotube membrane on a titanium substrate for delivery of a therapeutic agent. The titania nanotube membrane is prepared by first growing the titania nanotubes on a titanium substrate, and then etching the backside of the titanium substrate, the side without the nanotubes, until the inner portion of the nanotubes is exposed of a first group of the titania nanotubes. The titania nanotube membrane can also include a second group of the titania nanotubes where the first end of the titania nanotubes remains closed. The narrow diameter of the titania nanotubes controls the release of the therapeutic agent in the drug delivery device because the titania nanotubes are the only pathway for diffusion out of the device. The release rate of the therapeutic agent can be zero-order.

II. Definitions

"Therapeutic agent" refers to any agent capable of providing a therapeutic response, such as a drug or biologic.

"Titania nanotube membrane" refers to an array of titania nanotubes on a titanium substrate where at least a portion of the titania nanotubes are open at both ends and capable of allowing diffusion of liquids or solids from one side of the membrane to the other through the titania nanotubes.

"Fluid contact" refers to the contents of the reservoir being able to diffuse from the reservoir to the titania nanotubes. The contents of the reservoir can be in liquid form, but can also be in powder or solid form.

"Aspect ratio" refers to the ratio of length to diameter of the titania nanotubes, including the internal and external diameter.

"Zero-order rate of release" refers to the rate of release that is independent of concentration of the therapeutic agent in the reservoir.

"Contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

"Halogen ion" refers to fluoride, chloride, bromide and iodide ions. The halogen ion can be paired with a suitable counterion, such as ammonium.

"Water-miscible solvent" refers to a solvent that is at least partially miscible with water, and can be completely miscible with water.

III. Device

The present invention provides a drug delivery device having a titania nanotube membrane on a titanium substrate providing the only diffusion pathway for any therapeutic agent out of the device.

In some embodiments, the present invention provides a device having a capsule suitable for implantation. The device also includes a reservoir encapsulated by the capsule, wherein the reservoir is suitable for containing a therapeutic agent. The device also includes a titania nanotube membrane on a titanium substrate, wherein the titanium substrate is attached to the capsule such that the titanium substrate is in contact with the reservoir, wherein the titania nanotube membrane comprises a plurality of titania nanotubes in fluid contact with the reservoir. The device is such that the plurality of titania nanotubes is the only diffusion pathway out of the reservoir for the therapeutic agent.

The capsule (100) of FIG. 1 can be any capsule that is biocompatible with the body. The capsule can be prepared from any suitable material such as metals, polymers and combinations thereof. Useful metals can be pure metals or alloys, and include, but are not limited to, titanium and steel. Polymers useful in the present invention include any natural or synthetic polymer that is biocompatible with the body. In some embodiments, the capsule includes titanium.

The capsule can have any suitable shape or size. The capsule can be spherical, elliptical, oblong, circular, or cylindrical, among others.

The device also includes the reservoir (110) of FIG. 1 which contains the therapeutic agent. Any therapeutic agent is useful in the device of the present invention. Useful therapeutic agents include drugs and biologics. Suitable therapeutic agents include biologically active macromolecules such as peptides, protein drugs, or polynucleic acids. Suitable peptides or protein biopharmaceuticals include: hormones, hormone agonists, hormone antagonists, growth factors such as CSF, EPO, and growth hormone, cytokines such as the interleukins, immune modulators such as interferon gamma and interferon beta, anti-infectives such as interferon alpha 2b, anti-inflammatories, immune suppressant/anti-rejection drugs, antibodies, anti-arthritic drugs, and anti-tumor agents. Suitable polynucleic acids include: DNA, RNA, plasmid molecules, antisense DNA, and ribozymes. Small molecular weight molecules are also compatible with the present invention. Suitable small molecular weight molecules include, but are not limited to, pain medications or anti-psychotic agents.

Preferably, stabilizers co-formulated with the therapeutic agent contained within the reservoir include water miscible solvents, or polymers. Suitable stabilizers include, but are not limited to carbohydrates, sugars, dextrans, polyvinyl pyrrolidone, gum arabic, polyethylene glycol, albumin, dendritic polymers, cross-linked polymer matrix, and surfactants. Representative sugars include trehalose, glucose and sucrose.

In some embodiments, the therapeutic agent can be beta-glucocerobrosidase, interferon alpha, interferon beta, agasidase alpha, agasidase beta, exenatide, nutropin/somatropin, factor VIII, fondaparinux, aldesleukinand, risperidone, forigerimod, NP fusion proteins, IL-12, a melanocyte stimulating hormone, or bapineuzumab. Analogues of these therapeutic agents are also contemplated. In some embodiments, the therapeutic agent is interferon alpha.

The therapeutic agent can be in any suitable form in the reservoir, such as a liquid, a solid or a suspension. Solid forms include, but are not limited to, powders and micronized particles. For example, the powder can be lyophilized.

The titanium substrate (130) of FIG. 1 can be attached to the capsule by any suitable methods in the art. For example, the titanium substrate can be laser welded to the capsule.

The titania nanotubes (121) of FIG. 1 can have any suitable dimensions, including the internal diameter, the length and the aspect ratio. The internal diameter can be from about 1 nm to about 1000 nm, and can be the same or variable along the length of the titania nanotube. When the internal diameter is variable, the internal diameter can increase from one end of the titania nanotube to the other. For example, the internal diameter of the titania nanotube at the end in contact with the reservoir can be smaller than at the end opposite the reservoir, where the internal diameter increases gradually along the length of the titania nanotube. The internal diameter can be about 1, 2, 3, 4, 5, 6, 7, 8, 9, 10, 15, 20, 25, 50, 75, 100, 200, 300, 400, 500 or 1000 nm. The internal diameter can be of from about 1 to 1000 nm, or from about 1 to about 100 nm, or from about 1 to about 50 nm, or from about 1 to about 20 nm. In some embodiments, the internal diameter can be of from about 10 nm to about 1000 nm.

The titania nanotubes can have any suitable length. For example, the titania nanotubes can be from about 100 nm to about 100 µm, or about 500 nm, 1 µm, 5, 10, 20, 30, 40, 50, 60, 70, 80, 90 or 100 µm. In some embodiments, the titania nanotubes have a length of about 1 µm to about 100 µm.

The titania nanotubes can also have any suitable aspect ratio, defined by the length of the titania nanotube divided by the internal or external diameter. The aspect ratio can be from about 10 to about 10,000, or from about 10 to about 1,000. Other aspect ratios include, but are not to, about 50, 100, 200, 300, 400, 500, 600, 700, 800, 900, 1000, 2000, 3000, 4000, 5000, 6000, 7000, 8000, 9000, or 10,000.

The titania nanotubes are in fluid contact with the reservoir such that the therapeutic agent, whether in liquid, solid or suspension form, can diffuse from the reservoir and into the titania nanotubes at the titanium substrate, followed by exiting the titania nanotubes at the opposite end and entering the body. The rate of release of the therapeutic agent can be any suitable rate of release, such as zero-order rate of release. In some embodiments, the release of the therapeutic agent from the reservoir and through the titania nanotube membrane is a zero-order rate of release.

The titania nanotube membrane can be prepared by any suitable method. In some embodiments, the titania nanotube membrane is prepared by the method of the present invention.

IV. Preparation of Titania Nanotube Membrane

The titania nanotube membrane of the device of the present invention can be prepared by any suitable method, namely by growing the titania nanotubes on a titanium substrate, followed by etching the back side of the titanium substrate, the side opposite the titania nanotubes, until the inner portion of a subset of the nanotubes is exposed. In some embodiments, the present invention provides a method of preparing a titania nanotube membrane, the method including growing a plurality of titania nanotubes on a first side of a titanium substrate under anodization conditions, such that a first end of each nanotube is closed and attached to the titanium substrate and a second end of each nanotube is open. The method also includes etching the titanium substrate on the side opposite the first side, under conditions sufficient to open the first end of a first group of the titania nanotubes, thereby preparing the titania nanotube membrane.

The titania nanotube membrane can be a continuous membrane of titania nanotubes, or can be patterned. The patterned titania nanotube membrane has regions of titania nanotubes and regions of titanium. The patterned titania nanotube membrane can have any type of pattern, such as lines, checkerboard, etc.

The titania nanotube membrane prepared by the method of the present invention can have all the titania nanotubes open at both ends, or have only a portion of the titania nanotubes open at both ends. For example, the titania nanotube membrane can have a first group of titania nanotubes open at the first and second ends of the titania nanotubes. The first group of nanotubes can be all of the nanotubes in the titania nanotube membrane, or a subset of the titania nanotubes in the membrane. When the first group of titania nanotubes is not all of the titania nanotubes in the membrane, the titania nanotube membrane also includes a second group of titania nanotubes where the first end remains closed. In some embodiments, the first end of a second group of the titania nanotubes remains closed. The titania nanotube membrane can include other groups of titania nanotubes.

The anodization conditions include any conditions capable for growing titania nanotubes. In some embodiments, growing titania nanotubes includes contacting the first side of the titanium substrate with an anodization solution having a halogen ion, water and a water-miscible solvent.

The titanium substrate can be of any suitable thickness, such as a thickness where an additional substrate or support is not needed to prepare the titania nanotube membrane or support the titania nanotube membrane in the device described above.

The halogen ion can be fluoride, chloride, bromide or iodide. In some embodiments, the halogen ion can be fluoride. In some embodiments, the anodization solution includes ammonium fluoride.

The water-miscible solvent can be any solvent miscible in water. In some embodiments, the water-miscible solvent can be ethanol, ethylene glycol, propylene glycol or 1,3-propanediol. In some embodiments, the water-miscible solvent can be ethylene glycol. The water-miscible solvent present in the anodization solution can be present in any suitable amount. For example, the water-miscible solvent can be present in an amount such as 50, 55, 60, 65, 70, 75, 80, 85, 90, 91, 92, 93, 94, 95, 96, 97, 98 or 99 wt %. In some embodiments, the water-miscible solvent can be present in an amount of from about 50 to about 99 wt %. In some embodiments, the water-miscible solvent can be present in an amount of from about 95 to about 99 wt %.

The anodization solution includes any suitable amount of the halogen ion, water and water-miscible solvent. For example, ammonium fluoride as the halogen ion can be present in an amount of from about 0.01 to about 10 wt %, or about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0 or 10.0 wt %. In some embodiments, the ammonium fluoride can be present in an amount of from about 0.01 to about 5 wt %. In some embodiments, the ammonium fluoride can be present in an amount of from about 0.1 to about 1 wt %. In some embodiments, the ammonium fluoride can be present in an amount of about 0.3 wt %.

The water present in the anodization solution can be present in any suitable amount. For example, water can be present in an amount such as 0.1, 0.5 1, 2, 3, 4, 5, 10, 20, 30, 40 or 50 wt %. In some embodiments, the water is present in an amount of from about 0.1 to about 50 wt %. In some embodiments, the water is present in an amount of from about 0.1 to about 5 wt %.

In some embodiments, the anodization solvent includes ammonium fluoride in an amount from about 0.1 to about 1 wt %, water in an amount of from about 1 to about 5 wt %, and the water-miscible solvent in an amount of from about 95 to about 99 wt %.

In some embodiments, the method of making the titania nanotube membrane also includes annealing the titania nanotubes on the titanium substrate. The annealing can be performed at any suitable temperature for any suitable period of time. In some embodiments, the annealing step includes heating the plurality of titania nanotubes on the titanium substrate at a temperature of from about 200° C. to about 1000° C. Other temperatures useful in the annealing step include, but are not limited to, 200, 250° C., 300, 350, 400, 450, 500, 600, 700, 800, 900 or 1000° C. In some embodiments, the temperature can be of from about 300° C. to about 600° C., or from about 400° C. to about 500° C. In some embodiments, the temperature can be about 450° C.

The etching can be performed by any suitable etching method. For example, the etching can be a plasma etch, or a reactive-ion etch such as a chlorine deep reactive-ion etch.

In another embodiment, the present invention provides a titania nanotube membrane prepared by the process above.

In another embodiment, the present invention provides a titania nanotube membrane having a plurality of titania nanotubes on a titanium substrate, wherein each nanotube has a first and a second end such that both the first and second ends of a first group of the titania nanotubes are opens. In some embodiments, the titania nanotube membrane further comprises a second group of the titania nanotubes wherein only the first ends are open. In some embodiments, the titania nanotube membrane can be prepared by the process described above.

V. Examples

Example 1: Nanotube Fabrication on Patterned Disks

General

Reagents and patterned disks are inspected prior to use. Material safety data sheets (MSDS) for ammonium fluoride ($NH_4F$) and mild hydrofluoric acid are reviewed, and proper safety equipment is used during handling of fluorine and fluorine-contaminated materials to avoid exposure. The fluoride-containing salt used in the procedures is dissolved in water to become aqueous fluorine, which is toxic by ingestion, inhalation, and skin contact. 18.2 MΩ deionized water (referred to hereafter as "DI water") is used for all reagent preparation and equipment cleaning. Reagent solutions are neutralized at the end of each fabrication run.

Nanotube Fabrication Assembly Set-Up

Figure 2:
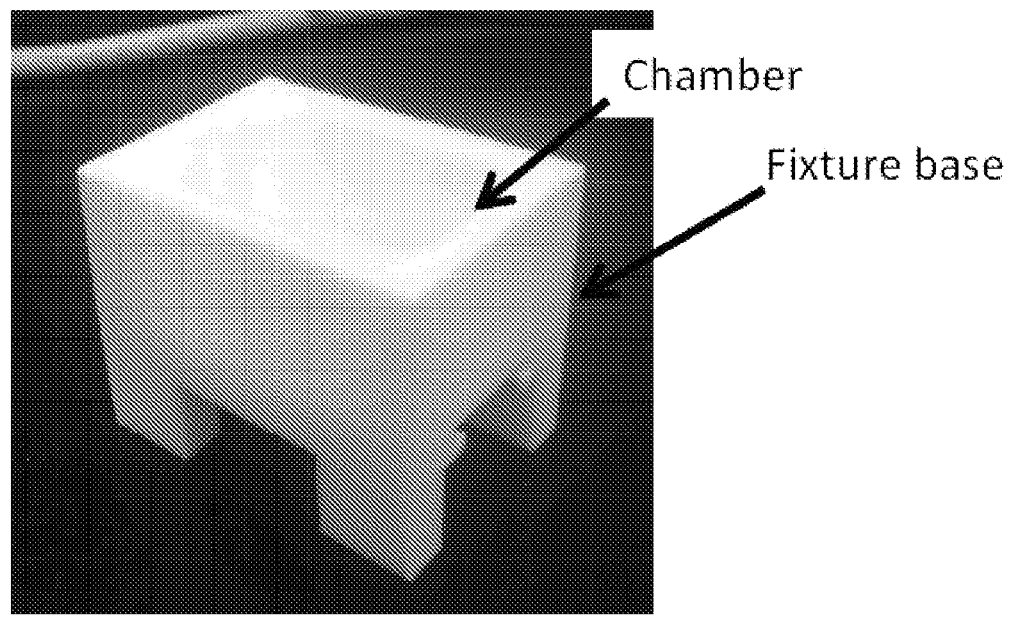
FIG. 2 shows the chamber used for nanotube fabrication on a fixture base.
Figure 3:
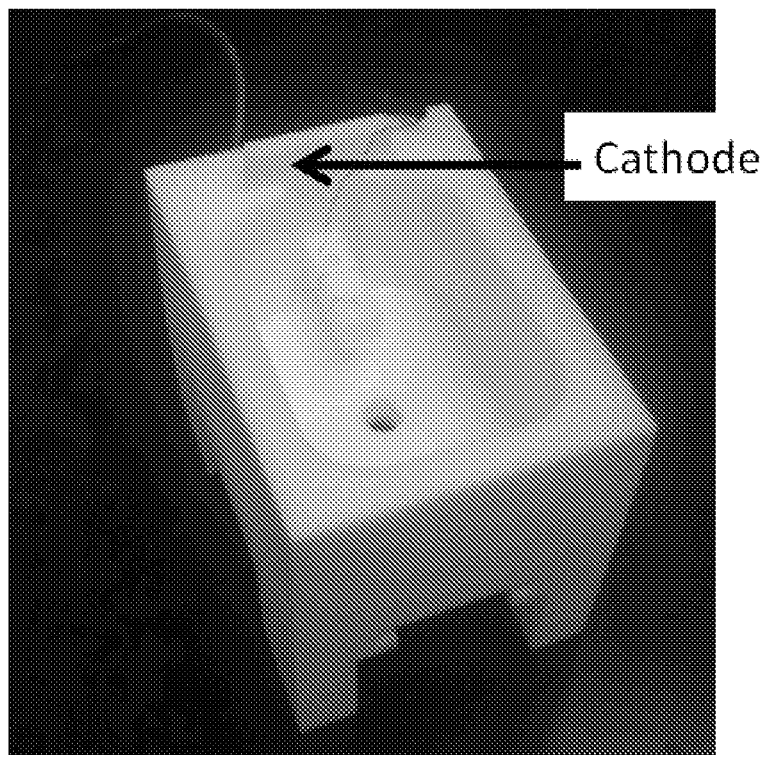
FIG. 3 shows the chamber with the cathode inserted in the groove in the chamber.
Figure 4:
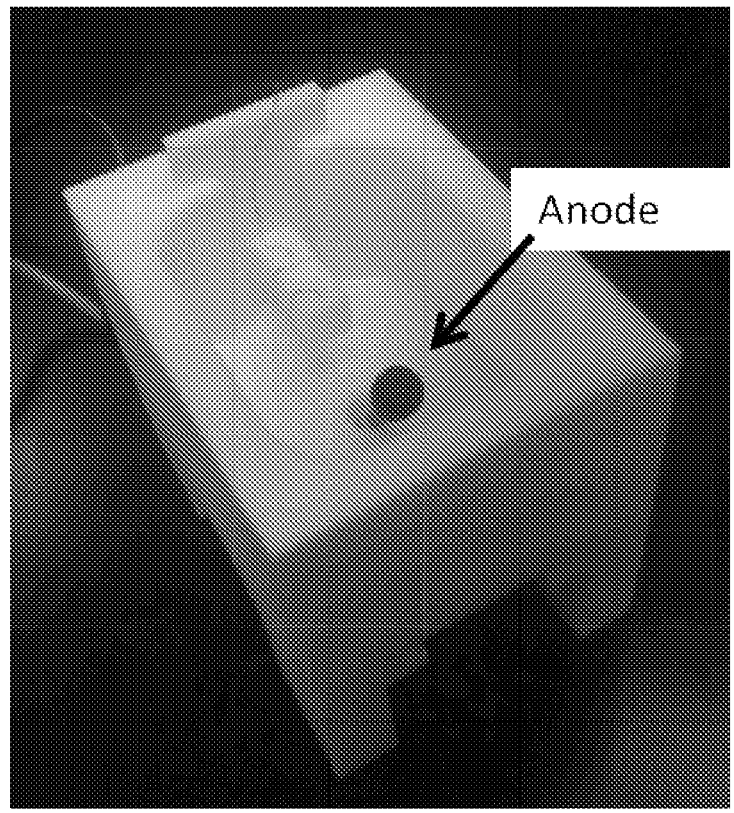
FIG. 4 shows the chamber with anode inserted in the hole in the base of the chamber with the gasket side of the anode remaining in the chamber.
Figure 5:
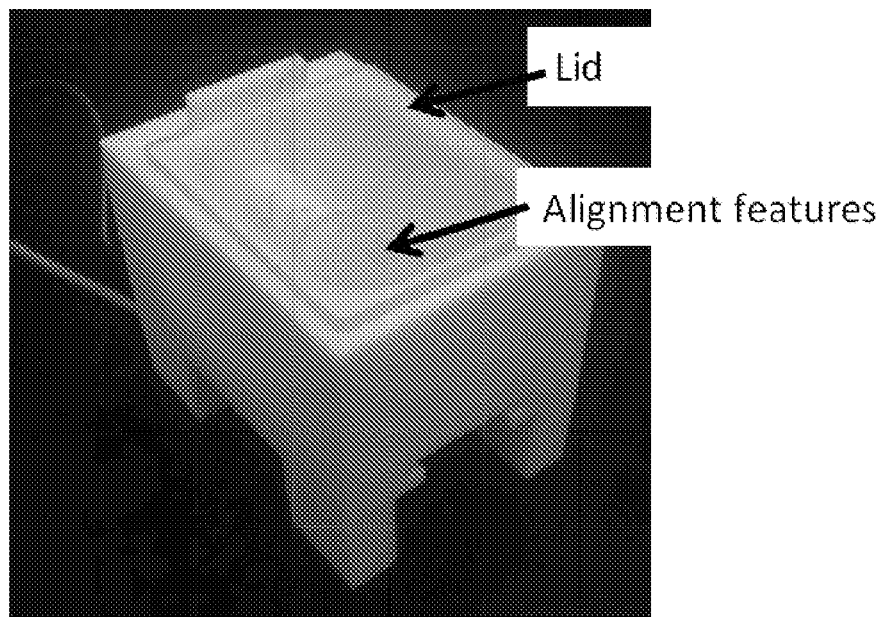
FIG. 5 shows the chamber with the lid placed with the cylinder alignment features inside the chamber.
Figure 6:
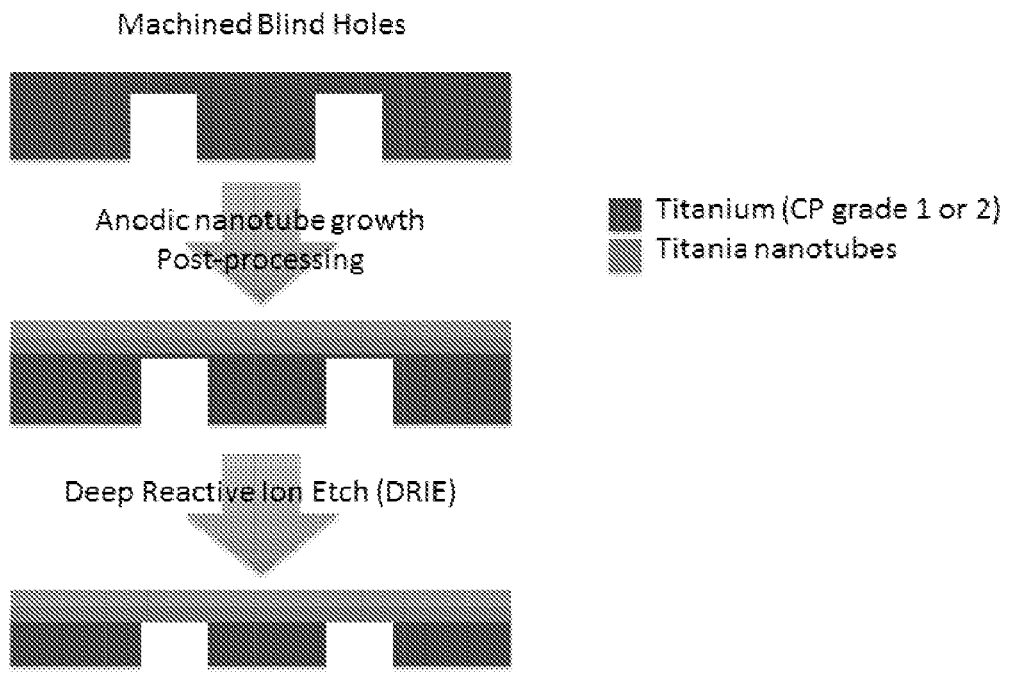
FIG. 6 shows a schematic for the method of the present invention, including preparation of a titanium substrate (CP grade 1 or 2) from which the titania nanotubes are grown, and then etching the titanium substrate to reveal the titania nanotube membrane.
Figure 7:
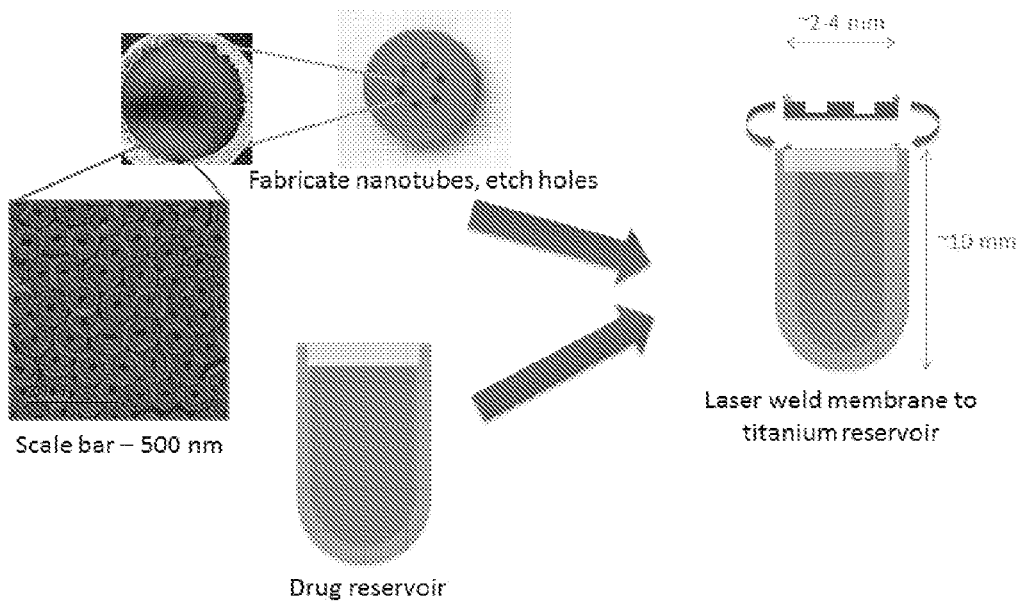
FIG. 7 shows additional details of the inventive device, including the titania nanotube membranes on the titanium substrate, and the laser welding of the titanium substrate to the reservoir, such that the only avenue for release of the reservoir contents is via the titania nanotube membrane.
Figure 8:
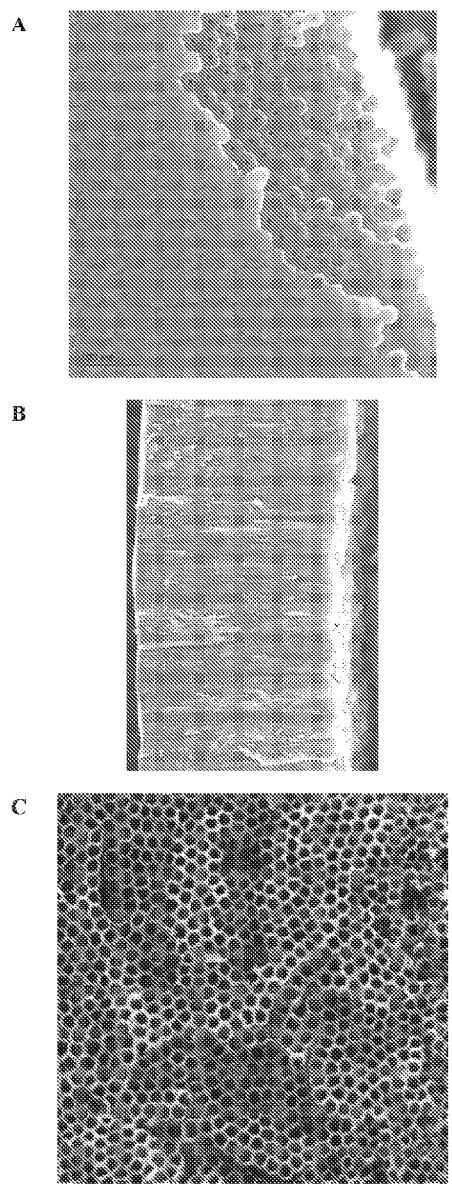
FIG. 8 shows titania nanotubes fabricated in the process of the present invention, including the bottoms of the nanotubes (A), side view showing ~60 micron length of the nanotubes (B), and the nanotube tops (C).

The fixture is placed in an upright position (FIG. 2). The cathode is inserted by sliding it into the groove in the chamber of the fixture until seated (FIG. 3). The anode is inserted by pushing the wire through the hole in the base of the chamber; the gasket side of the anode should remain in the chamber (FIG. 4). If necessary, the lid is placed with the cylinder alignment features inside the chamber (FIG. 5). The fixtures are exposed to potentially toxic aqueous fluorine ions during use. Therefore, fixtures should be appropriately cleaned and gloves and safety goggles should be used during assembly and handling.

Anodization Solution Preparation

A solution of 0.3 wt % ammonium fluoride in aqueous 98% (v/v) ethylene glycol (EG) is prepared by dissolving 3+/−0.1 g of $NH_4F$ in 20+/−0.25 mL of $H_2O$ in a 1-liter HDPE bottle. After complete dissolution of $NH_4F$, 980+/−5 of EG is added to the solution.

Cleaning

The patterned disks are cleaned via sonication in an aqueous 10% (v/v) Micro-90 solution (Aldrich) for 6 minutes. The disks are removed from the sonication bath, rinsed with $H_2O$ followed by ethanol, and dried under a stream of nitrogen. The fabrication fixture and platinum wire may be cleaned in a similar manner if necessary. For convenience, the patterned disks may be left in the sonication bath until set-up of the nanotube fabrication assembly is complete.

Run Set-Up

The power supplies for the nanotube fabrication assembly are turned on and set to 60 V+/−0.1 V. Run parameters are set by the user using the software interface:
1. The program is started by pressing the arrow key.
2. Run time (e.g. 18 hours) is entered in the "Hours" text box for each run.
3. The file name for the first run is assigned by opening the appropriate folder in the file browser and selecting the most recent run. The file name is copied and pasted in the file path for the each run, and the filenames are then edited to reflect the correct run numbers.
4. Run parameters are entered in the tube in Excel.

The nanotube fabrication fixture is placed into the secondary containment, and the patterned disk is firmly pressed into the Viton gasket with the machined windows facing down until it seats. The disks should be level with the work surface. Electrical conductivity is confirmed using an ohmmeter. The anode and cathode are connected to the corresponding quick-disconnect power leads. The fixture chamber is filled with 30 mL of the anodization solution, prepared as described above. The fixtures are covered with lids such that cylinder alignment features are inside the chamber. The thermistors are cleaned with an ethanol-soaked wipe and inserted through the lids into the solution.

Run

Recording of each run is initiated by pressing the "Begin Run" button on the software interface. The commencement of tube growth is indicated by current spike and decay. After the full duration of the run time as entered during run set-up, the run record should be reviewed to ensure that power did not fail during the run. Temperature and current fluctuations are recorded; large current fluctuations may indicate a physical disturbance during the run. The program is ended by pressing the "Stop" button, and cleaning of the assembly is conducted immediately.

Cleanup

The power supply is turned off and the leads to the fabrication fixture are disconnected after the relays have opened and a drop in current is registered. The remaining anodization solution is poured from the assembly into a beaker containing roughly 1-1.5 grams of calcium carbonate. While removing the anodization solution, the fabrication fixture is thoroughly rinsed with ethanol by spraying with an ethanol spray bottle at least 8 times. All ethanol rinses are collected in a waste beaker, and the ethanol rinse is repeated. Additional ethanol is sprayed into the assembly so that the disk and a few millimeters of the chamber are covered, and the fixtures are covered with the lids again. The fixtures may be left in this state for up to a maximum of 24 hours if necessary.

The time at which the anodization solution was removed from the disks is recorded. The disks and solution are inspected in terms of color, pattern, or other markings. The fixture lids are placed in a stainless steel pan containing ethanol. The fixture itself is placed sideways in the pan, so that the disk stays submerged in ethanol. The Viton gasket/wire assembly is pushed out of the bottom of the fabrication fixture while keeping the disk submerged in ethanol. The disk is carefully removed by pressing the base of the gasket and/or pulling the gasket sides back so that the disk pops out. The disk is cleaned with ethanol, dried in air, placed in a gel pak, and labeled. Both sides of the gel paks are scanned. Each fabrication fixture and cathode insert are dried separately with nitrogen and placed in a clean screw-top container. Tweezers and secondary containment are rinsed with water and dried with nitrogen or allowed to air dry. The neutralized anodization solution is flushed in a sink with several liters of water (a faucet is left running for 2-3 minutes).

Example 2: Nanotube Annealing

General

The annealing procedure involves the use of a high-temperature furnace. The furnace must be cool enough to work with (e.g. room temperature) prior to removing parts or otherwise preparing the instrument. Proper safety equipment includes tweezers or tongs, closed toe shoes, and heat resistant gloves. After annealing, patterned disks with nanotubes are stabilized for use in water and cleaned of tube debris.

Preparing Disk for Annealing

Patterned disks are inserted into an appropriate furnace (e.g. Isley Vulcan 3-550) with the disks centered. The furnace is programmed by the user with the following parameters.
   a. Duration: 1 hour
   b. Ramp rate: 10° C./min
   c. Temperature: 450° C.

d. Ensure that the second and third ramps are to 450° C., and are for 0 minutes
e. The cycle should be 1 hr and 42 minutes long.

The furnace door is closed and the anneal is started by pressing the start button.

Removing Disks from Annealing Furnace

Within 15 minutes after the anneal is complete, the furnace door is opened and allowed to cool to 280° C. or lower before continuing. The disks are transferred to an aluminum cooling block using tweezers. The disks are removed to aluminum foil to finish cooling. The cooled disks are then placed in labeled gel paks, and the front and back of each gel pak are scanned.

Post-Processing

Each disk is cleaned with ethanol, dried in air, and returned to the gel pak. The font and back of each gel pak are scanned. Nanotube annealing is typically followed by nanotube etching.

Example 3: Nanotube Etching

Titanium Etch Jig Assembly Set-Up

Titanium etch jigs are sonicated in Micro-90 solution. The etch jigs are rinsed with deionized water followed by ethanol and dried under a stream of nitrogen. The etch jigs are deburred if necessary. The jig is squeezed radially to plastically reduce the gap using a pair of clean needle-nose pliers. The jig is spread with a spreader tool, and the patterned disk with nanostructures is inserted. The bottom of the jig is labeled with the run number and placed in a gel pak.

Disk Etching

Disk etching is conducted with a transformer-coupled plasma (TCP) etcher (e.g. Lam Research TCP 9600SE II). The etch jigs are attached to a 6" silicon oxide wafer using 0.005" adhesive-backed Kapton. The bottom of the wafer is cleaned by blowing with a stream of nitrogen before placing the wafer into the entry wafer cassette of the TCP etcher. Argon is used in the inert gas line, and the chiller temperature is set to 15° C. The appropriate etching program is programmed by the user, having the following parameters: 400 W Source Power, 100 W Bias, 18.75 mT Chamber Pressure, 120 sccm $Cl_2$, and 15 sccm Ar.

A total of 60 minutes of etch is performed in 5 minute on-cycle (with 5 minute off-cycle with no RF, chamber pressure of 60 mT, 500 sccms Ar). The etch jigs are mounted using Kapton tape on a silicon wafer which had an oxide layer grown in the furnace for extended durations. The etching process is initiated by the user via software controls, and proper wafer feeding into the etcher is confirmed. The etching process is typically conducted over 120 minutes and is automatically controlled by the instrument. The wafer is removed from the exit cassette when the instrument idles after etching, and the jigs with patterned disks are removed from the wafer.

Example 4: Nanotube Fabrication on Patterned Disks

General

Reagents and patterned disks are inspected prior to use. Material safety data sheets (MSDS) for ammonium fluoride ($NH_4F$) and mild hydrofluoric acid are reviewed, and proper safety equipment is used during handling of fluorine and fluoride-contaminated materials to avoid exposure. The fluoride-containing salt used in the procedures is dissolved in water to become aqueous fluorine, which is toxic by ingestion, inhalation, and skin contact. 18.2 MΩ deionized water (referred to hereafter as "DI water") is used for all reagent preparation and equipment cleaning. Reagent solutions are neutralized at the end of each fabrication run.

Nanotube Fabrication Assembly Set-Up

The fixture is placed in an upright position (FIG. 2). The cathode is inserted by sliding it into the groove in the chamber of the fixture until seated (FIG. 3). The anode is inserted by pushing the wire through the hole in the base of the chamber; the gasket side of the anode should remain in the chamber (FIG. 4). If necessary, the lid is placed with the cylinder alignment features inside the chamber (FIG. 5). The fixtures are exposed to potentially toxic aqueous fluorine ions during use. Therefore, fixtures should be appropriately cleaned and gloves and safety goggles should be used during assembly and handling.

Anodization Solution Preparation

A 500 mL solution of 0.3 wt % ammonium fluoride in 2% DI water 98% ethylene glycol (EG) (v/v) is prepared by dissolving 1.5+/−0.1 g of $NH_4F$ in 10+/−0.25 mL of DI $H_2O$ in a 1-liter HDPE bottle. After complete dissolution of $NH_4F$, 490+/−5 mL of EG is added to the solution.

Cleaning

The patterned disks and stainless steel wire are cleaned via sonication in a solution of 10% Micro-90/90% water (vv) for 10 minutes. The disk and wire are removed from the sonication bath and rinsed with DI water. The disk is air dried, while the fabrication fixtures and stainless steel wires are dried with nitrogen. For convenience, the patterned disks may be left in the sonication bath until set-up of the nanotube fabrication assembly is complete.

Run Set-Up

The power supplies for the nanotube fabrication assembly are turned on and set to 60 V+/−0.1 V. Run parameters are set by the user using the software interface:

1. The program is started by pressing the arrow key.
2. Run time (e.g. 18 hours) is entered in the "Hours" text box for each run.
3. The file name for the first run is assigned by opening the appropriate folder in the file browser and selecting the most recent run. The file name is copied and pasted in the file path for the each run, and the filenames are then edited to reflect the correct run numbers.
4. Run parameters are entered in the tube table in Excel.

The nanotube fabrication fixture is placed into the secondary containment. The anode and cathode are connected to the corresponding quick-disconnect power leads. The patterned disk is firmly pressed into the Viton gasket with the machined windows facing down until it seats. The disks should be level with the work surface. Electrical conductivity is confirmed using an ohmmeter. The disk is wetted with ethanol (<100 μL). The fabrication fixture chamber is filled with 30+/−0.25 mL of the anodization solution, prepared as described above. The fixtures are covered with lids such that cylinder alignment features are inside the chamber.

Run

Recording of each run is initiated by pressing the "Begin Run" button on the software interface. The commencement of tube growth is indicated by current spike and decay. After the full duration of the run time as entered during run set-up, the run record should be reviewed to ensure that power did not fail during the run. Temperature and current fluctuations are recorded; large current fluctuations may indicate a physical disturbance during the run. The program is ended by pressing the "Stop" button, and cleaning of the assembly is conducted immediately.

Cleanup

Partially fill 5 mL tubes with ethanol (approximately 2 sprays from the bottle). The power supply is turned off and the leads to the fabrication fixture are disconnected after the relays have opened and a drop in current is registered. The remaining ethylene glycol solution is poured from the assembly into a beaker containing roughly 1-1.5 grams of calcium carbonate. While removing the ethylene glycol solution, the fabrication fixture is thoroughly rinsed with ethanol by spraying with an ethanol spray bottle at least 8 times. All ethanol rinses are collected in a waste beaker, and the ethanol rinse is repeated. Additional ethanol is sprayed into the assembly so that the disk and a few millimeters of the chamber are covered, and the fixtures are covered with the lids again. The fixtures may be left in this state for up to a maximum of 24 hours if necessary.

The time at which the anodization solution was removed from the disks is recorded. The disks and solution are inspected in terms of color, pattern, or other markings. The fixture lids are placed in a tube containing ethanol. The fixture itself is placed sideways in the pan, so that the disk stays submerged in ethanol. The Viton gasket/wire assembly is pushed out of the bottom of the fabrication fixture while keeping the disk submerged in ethanol. The disk is carefully removed by pressing the base of the gasket and/or pulling the gasket sides back so that the disk pops out. The disk is placed nanotube side down into a 5-ml tube partially filled with ethanol and sonicated for 15 minutes. The disk is removed from the tube and sprayed several limes with ethanol. The disk is transferred directly to a hotplate at 100° C. to dry. The disk is removed when dry (usually after 30-60 s on the hotplate). The disk is allowed to cool, placed in a gel pak, and labeled. Both sides of the gel pales are scanned. Each fabrication fixture and cathode insert are dried separately with nitrogen and placed in a clean screw-top container. Tweezers and secondary containment are rinsed with water and dried with nitrogen or allowed to air dry. The neutralized anodization solution is flushed in a sink with several liters of water (a faucet is left running for 2-3 minutes).

Example 5: Nanotube Fabrication on Patterned Disks

General

Reagents and patterned disks are inspected prior to use. Material safety data sheets (MSDS) for ammonium fluoride ($NH_4F$) and mild hydrofluoric acid are reviewed, and proper safety equipment is used during handling of fluorine and fluorine-contaminated materials to avoid exposure. The fluoride-containing salt used in the procedures is dissolved in water to become aqueous fluorine, which is toxic by ingestion, inhalation, and skin contact. 182 MΩ deionized water (referred to hereafter as "DI water") is used for all reagent preparation and equipment cleaning. Reagent solutions are neutralized at the end of each fabrication run.

Nanotube Fabrication Assembly Set-Up

The fixture is placed in an upright position (FIG. 2). The cathode is inserted by sliding it into the groove in the chamber of the fixture until seated (FIG. 3). The anode is inserted by pushing the wire through the hole in the base of the chamber; the gasket side of the anode should remain in the chamber (FIG. 4). If necessary, the lid is placed with the cylinder alignment features inside the chamber (FIG. 5). The fixtures are exposed to potentially toxic aqueous fluorine ions during use. Therefore, fixtures should be appropriately cleaned and gloves and safety goggles should be used during assembly and handling.

Anodization Solution Preparation

A solution of 1.0 wt % ammonium fluoride in aqueous 98% (v/v) ethylene glycol (EG) is prepared by dissolving 7.5+/−0.005 g of $NH_4F$ in 15+/−0.1 mL of $H_2O$ in a 1-liter HDPE bottle, After complete dissolution of $NH_4F$, 980+/−5 mL of EG is added to the solution.

Cleaning

The patterned disks are cleaned via sonication in an aqueous 10% (v/v) Micro-90 solution (Aldrich) for 6 minutes. The disks are removed from the sonication bath, rinsed with $H_2O$ followed by ethanol, and dried under a stream of nitrogen. The fabrication fixture and platinum wire may be cleaned in a similar manner if necessary. For convenience, the patterned disks may be left in the sonication bath until set-up of the nanotube fabrication assembly is complete.

Run Set-Up

The power supplies for the nanotube fabrication assembly are turned on and set to 50 V+/−0.1 V. Run parameters are set by the user using the software interface:

1. The program is started by pressing the arrow key.
2. Run time (e.g. 18 hours) is entered in the "Hours" text box for each run.
3. The file name for the first run is assigned by opening the appropriate folder in the file browser and selecting the most recent run. The file name is copied and pasted in the file path for the each run, and the filenames are then edited to reflect the correct run numbers.
4. Run parameters are entered in the tube table in Excel.

The nanotube fabrication fixture is placed into the secondary containment, and the patterned disk is firmly pressed into the Viton gasket with the machined windows facing down until it seats. The disks should be level with the work surface. Electrical conductivity is confirmed using an ohmmeter. The anode and cathode are connected to the corresponding quick-disconnect power leads. The fixture chamber is filled with 30 mL of the anodization solution, prepared as described above. The fixtures are covered with lids such that cylinder alignment features are inside the chamber. The thermistors are cleaned with an ethanol-soaked wipe and inserted through the lids into the solution.

Run

Recording of each run is initiated by pressing the "Begin Run" button on the software interface. The commencement of tube growth is indicated by current spike and decay. After the full duration of the run lime as entered during run set-up, the run record should be reviewed to ensure that power did not fail during the run. Temperature and current fluctuations are recorded; large current fluctuations may indicate a physical disturbance during the run. The program is ended by pressing the "Stop" button, and cleaning of the assembly is conducted immediately.

Cleanup

The power supply is turned off and the leads to the fabrication fixture are disconnected after the relays have opened and a drop in current is registered. The remaining anodization solution is poured from the assembly into a beaker containing roughly 1-1.5 grains of calcium carbonate. While removing the anodization solution, the fabrication fixture is thoroughly rinsed with isopropanol by spraying with a spray bottle at least 8 times. All isopropanol rinses are collected in a waste beaker, and the isopropanol rinse is repeated. Additional isopropanol is sprayed into the assembly so that the disk and a few millimeters of the chamber are covered, and the fixtures are covered with the lids again. The fixtures may be left in this state for up to a maximum of 24 hours if necessary.

The time at which the anodization solution was removed from the disks is recorded. The disks and solution are inspected in terms of color, pattern, or other markings. The Viton gasket/wire assembly is pushed out of the bottom of the fabrication fixture while keeping the disk wet with isopropanol. The disk is carefully removed by pressing the base of the gasket and/or pulling the gasket sides back so that the disk pops out. The disk is cleaned with isopropanol, sonicated in isopropanol (10 minutes, followed by another 5 minutes in fresh isopropanol), dried in air, placed in a gel pak, and labeled. Both sides of the gel paks are scanned. Each fabrication fixture and cathode insert are dried separately with nitrogen and placed in a clean screw-top container. Tweezers and secondary containment are rinsed with water and dried with nitrogen or allowed to air dry. The neutralized anodization solution is flushed in a sink with several liters of water (a faucet is left running for ~2-3 minutes).

Example 6: Nanotube Etching

Using the same titanium etch jig assembly described in example 3, disk etching is conducted with a transformer-coupled plasma (TCP) etcher (e.g. Lam Research TCP 9600SE II). The etch jigs are attached to a 6" silicon wafer using a thermal coupling fluid. The bottom of the wafer is cleaned by blowing with a stream of nitrogen before placing the wafer into the entry wafer cassette of the TCP etcher. The chiller temperature is set to 15° C.

Prior to etching the titanium, any titanium oxide on the unanodized side of the substrate is removed via $CF_4$ etch. A total of 75 minutes of etch is performed to remove the titanium and expose the titania nanotubes using the following parameters: 400 W Source Power, 100 W Bias, 18.75 mT Chamber Pressure, 100 sccm $Cl_2$. Any residual chlorine is then removed by oxygen plasma.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of preparing a titania nanotube membrane, the method comprising:
   growing a plurality of titania nanotubes on a first side of a titanium substrate under anodization conditions, such that a first end of each nanotube is closed and directly attached to the titanium substrate, and a second end of each nanotube is open; and
   etching the titanium substrate on the side opposite the first side, under conditions sufficient to open the first end of a first group of the titania nanotubes, thereby preparing the titania nanotube membrane, wherein the nanotubes opened on the first end and the nanotubes opened on the second end is the only pathway for diffusion from one side of the titania nanotube membrane to the other, and wherein the first end of each nanotube is directly attached to the titanium substrate.

2. The method of claim 1, wherein the first end of a second group of the titania nanotubes remains closed.

3. The method of claim 1, wherein the growing step comprises:
   contacting the first side of the titanium substrate with an anodization solution comprising a halogen ion, water and a water-miscible solvent.

4. The method of claim 3, wherein the anodization solution comprises ammonium fluoride.

5. The method of claim 3, wherein the water-miscible solvent is selected from the group consisting of ethanol, ethylene glycol, propylene glycol, and 1,3-propanediol.

6. The method of claim 3, wherein the anodization solvent comprises ammonium fluoride in an amount of from about 0.01 to about 5 wt %.

7. The method of claim 3, wherein the anodization solvent comprises water in an amount of from about 0.1 to about 50 wt %.

8. The method of claim 3, wherein the anodization solvent comprises water-miscible solvent in an amount of from about 50 to about 99 wt %.

9. The method of claim 3, wherein the anodization solvent comprises
   ammonium fluoride in an amount from about 0.1 to about 1 wt %;
   water in an amount of from about 1 to about 5 wt %; and
   the water-miscible solvent in an amount of from about 95 to about 99 wt %.

10. The method of claim 1, wherein the method further comprises annealing the plurality of titania nanotubes on the titanium substrate.

11. The method of claim 10, wherein the annealing step comprises:
    heating the plurality of titania nanotubes on the titanium substrate at a temperature of from about 200 to about 1000° C.

12. The method of claim 11, wherein the heating is at a temperature of about 450° C.

13. The method of claim 1, wherein the etching is performed using a deep reactive-ion etch.

14. A titania nanotube membrane prepared by the process of claim 1, the process comprising:
    growing a plurality of titania nanotubes on a first side of a titanium substrate under anodization conditions, such that a first end of each nanotube is closed and directly attached to the titanium substrate and a second end of each nanotube is open; and
    etching the titanium substrate on the side opposite the first side, under conditions sufficient to open the first end of a first group of the titania nanotubes, thereby preparing the titania nanotube membrane, wherein the nanotubes opened on the first end and the nanotubes opened on the second end is the only pathway for diffusion from one side of the titania nanotube membrane to the other, and wherein the first end of each nanotube is directly attached to the titanium substrate.

15. A device comprising:
    a capsule suitable for implantation;
    a reservoir encapsulated by the capsule, wherein the reservoir is suitable for containing a therapeutic agent; and
    a titania nanotube membrane directly attached to a titanium substrate, wherein the titanium substrate is attached to the capsule such that the titanium substrate is in contact with the reservoir, wherein the titania nanotube membrane comprises a plurality of titania nanotubes directly attached to the titanium substrate and in fluid contact with the reservoir, and wherein the titania nanotube membrane is prepared by the method of claim 1, such that the plurality of titania nanotubes is the only diffusion pathway out of the reservoir for the therapeutic agent.

16. The device of claim 15, wherein the capsule comprises titanium.

17. The device of claim 15, wherein the titania nanotubes have an internal diameter of from about 10 nm to 1000 nm.

18. The device of claim 15, wherein the titania nanotubes have a length of about 1 μm to about 100 μm.

19. The device of claim 15, wherein the titania nanotubes have an aspect ratio of about 10 to about 10,000.

20. The device of claim 15, wherein the therapeutic agent is selected from the group consisting of beta-glucocerobrosidase, interferon alpha, interferon beta, agasidase alpha, agasidase beta, exenatide, nutropin/somatropin, factor VIII, fondaparinux, aldesleukinand, risperidone, forigerimod, NP fusion proteins, IL-12, a melanocyte stimulating hormone, and bapineuzumab.

21. The device of claim 15, wherein the therapeutic agent is interferon alpha.

22. The device of claim 15, wherein the release of the therapeutic agent from the reservoir and through the titania nanotube membrane is a zero-order rate of release.

23. A titania nanotube membrane comprising a plurality of titania nanotubes directly attached to a titanium substrate, wherein each nanotube has a first end and a second end such that both the first end and second end of a first group of the titania nanotubes are open, wherein the first group of nanotubes is the only pathway for diffusion from one side of the titania nanotube membrane to the other.

24. The titania nanotube membrane of claim 23, wherein the titania nanotube membrane further comprises a second group of the titania nanotubes each nanotube having a first end and a second end, wherein only the second end of the second group of the titania nanotubes are open.

25. The titania nanotube membrane of claim 23, wherein the titania nanotube membrane is prepared by the method of claim 1.

\* \* \* \* \*